US000001148H

United States Statutory Invention Registration [19]

[11] Reg. Number: H1148

Wakabayashi et al.

[43] Published: Mar. 2, 1993

[54] METHOD OF SEPARATING ACTIVATED HUMAN PROTEIN C

[76] Inventors: Kenji Wakabayashi, 5-18, Tamadaira 3-chome; Yoshihiko Sumi, 18-4, Tamadaira 3-chome, both of Hino-shi, Tokyo; Yataro Ichikawa, 11-7, Kotesashi-cho 2-chome, Tokorozawa-shi, Saitama-ken; Yoichi Sakata, 1-13-39, Hanakaki-cho, Oyama-shi, Tochigi-ken; Nobuo Aoki, 20-2-304, Hongo 4-chome, Bunkyo-ku, Tokyo, all of Japan

[21] Appl. No.: 815,870

[22] Filed: Jan. 3, 1992

Related U.S. Application Data

[63] Continuation of Ser. No. 181,424, Apr. 14, 1988.

[30] Foreign Application Priority Data

Apr. 17, 1987 [JP] Japan ..... 62-93377

[51] Int. Cl.[5] ..... C12Q 1/56

[52] U.S. Cl. ..... 435/13; 435/219; 435/815; 436/548

[58] Field of Search ..... 436/548; 435/13, 219, 435/815; 530/413, 830

[56] References Cited

U.S. PATENT DOCUMENTS 4,902,614 2/1990 Wakabayashi et al. ..... 435/7

FOREIGN PATENT DOCUMENTS 0118256 9/1984 European Pat. Off. .
0138222 4/1985 European Pat. Off. .
0205046 12/1986 European Pat. Off. .
0215548 3/1987 European Pat. Off. .

OTHER PUBLICATIONS

Kisiel, W. et al. 1976, 15 4893–4900.
FEBS Letters, vol. 191, No. 1, Oct. 1985, pp. 75–81, M. Laurell et al., "Characterization of Monoclonal Antibodies . . . ".
Journal of Biological Chemistry, vol. 262, No. 28, Oct. 5, 1987, pp. 13798–13804, K. Ohlin et al. "Calcium-Dependent interaction . . . ".

*Primary Examiner*—Robert L. Stoll
*Assistant Examiner*—Joseph D. Anthony

[57] ABSTRACT

A method of separating activated human protein C, which comprises bringing a mixture containing activated human protein C having a gamma-carboxyglutamic acid (Gla) domain in the presence of a calcium ion into contact with a fixed antibody comprising an insoluble carrier and fixed thereto an antibody to a complex of human protein C and a calcium ion bound to the Gla domain whereby the activated human protein C is captured by the fixed antibody in the form in which the calcium ion is bound to the Gla domain. A method is also provided for separating activated human protein C from a mixture containing human protein C and activated human protein C, which comprises bringing a first mixture containing human protein C and activated human protein C having a Gla domain into contact with a first fixed antibody comprising an insoluble carrier and fixed thereto a first antibody to human protein C but not to activated human protein C to form a second mixture substantially free from human protein C while the human protein C is captured by the first fixed antibody, and bringing the second mixture in the presence of a calcium ion into contact with a second fixed antibody comprising an insoluble carrier and fixed thereto a second antibody to a complex of human protein C and a calcium ion bound at the Gla domain, whereby the activated human protein C is captured by the second fixed antibody in the form in which the calcium ion is bound to the Gla domain.

9 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD OF SEPARATING ACTIVATED HUMAN PROTEIN C

This application is a continuation of now abandoned application Ser. No. 07/181,424, filed on Apr. 14, 1988.

This invention relates to a method of separating activated human protein C. More specifically, it relates to a method of separating activated human protein C by using an antibody to a complex of human protein C and a calcium ion bound to the gamma-carboxyglutamic acid (Gla) domain of the human protein C.

Protein C, a vitamin K-dependent plasma protein, plays an important role in a living organism as a control factor on coagulation and fibrinolytic systems. Protein C is a serine precursor of serine protease. Physiologically, it is activated by thrombin bound to thrombomodulin on the surface layer of the vascular endothelium to become activated protein C having anticoagulating and fibrinolysis promoting activities.

In the present specification, protein C is sometimes abbreviated "PC", and activated protein C, "activated PC".

The importance of the action of PC in the living body is observed in serious recurrent thromboembolism in a congenitally PC-deficient patient (Broekmans et al., New Eng. J. Med., 309, 340–344, 1983; Saligsorn et al., New Eng. J. Med., 310, 559–562, 1984). Prolongation of the coagulation time and a rise in fibrinolytic activity in blood were determined in an experiment in which purified bovine activated PC was administered to dogs (Comp et al., J. Clin. Inv, 68, 1221–1228, 1981) and an experiment in which purified human activated PC was administered to cats (Burdick et al., Thrombosis Research 45, 413–419, 1987). These experiments suggest a remedy for a derangement in coagulation and fibrinolysis by administering activated PC.

The recent advance in gene recombinant technology has made it possible to produce recombinant human PC by cloning human PC gene in animal cells, and considerations are being given to the possible utility of the produced human PC for the treatment of congenital PC-deficiency, thromboembolism, disseminated intravascular coagulation and myocardial infraction (see Japanese Laid-Open Patent Publication No. 205487/1986). As a therapeutic agent, PC may be administered as PC or as activated PC depending upon the condition to be treated.

For administration as activated PC, it is necessary to activate natural PC purified from plasma or a coagulation factor concentrate or recombinant human PC purified from the culture supernatant of animal cells using thrombin, thrombin-thrombomodulin complex, snake venom, etc. and isolate the resulting activated PC. For example, there have been reported a method which comprises activating purified human PC with bovine thrombin and purifying the activated PC using a SP-Sephadex C-50 column and a QAE-Sephadex Q50 (dextran ion exchanger) column (made by Pharmacia) (Comp et al., J. Clin. Invest., 68: 1221–1228, 1981), and a method which comprises binding purified bovine thrombin to purified rabbit thrombomodulin fixed to an insoluble carrier and contacting the carrier to which the thrombin-thrombomodulin complex is fixed with a solution of purified PC to obtain activated PC (see Japanese Laid-Open Patent Publication No. 205487/1986) These methods are disadvantageous in that much time is required for separating activated PC, a tiny amount of thrombin might be included in activated PC or a large quantity of purified human thrombin or purified thrombomodulin is required, and are not entirely satisfactory for preparing a large quantity of purified activated PC.

Monoclonal antibodies to human protein C have been proposed (Blood & Vessel, 1984, vol. 15, No. 2, pages 171–174; J. Biochem., vol. 97, No. 1, 1985, pages 127–138; and Japanese Laid-Open Patent Publication No. 120,825/1985). These documents disclose 13 monoclonal antibodies to human protein C in total. Six of these bind to the L-chain of protein C; five, to the H-chain of protein C; and two recognize an area between the L-chain and H-chain of protein C. A paper in the J. Biochem., vol. 97, No. 1, 1985, pages 127–138 states at the end: "Of the present antibodies produced, some might be conformation-specific antibodies directed toward the metal ion-dependent structure of the protein". This, however, is speculation. The summary of this paper further states: "antibodies specific for the light chain did not bind to the gamma-carboxyglutamic acid-domain". This paper does not describe the fact that such conformation-specific antibodies were actually obtained. Such a fact has neither been reported subsequently.

In addition, the binding sites of the above 13 monoclonal antibodies to human protein C are sites common to protein C and PIVKA (protein induced by vitamin K absence or antagonists)-PC. Accordingly, using these monoclonal antibodies, protein C and PIVAK-PC cannot be measured or distinguished.

FEBS Letters, vol. 191, No. 1, October 1985, 75–81 discloses four monoclonal antibodies against human protein C. Three of these bind to human protein C irrespective of the presence or absence of a calcium ion, and the remaining one antibody binds to human protein C in the presence of a calcium ion but does not substantially bind to human protein C in the absence of a calcium ion. This paper also discloses that all of the above three antibodies have epitopes in the activation peptide region of human protein C.

Co-pending U.S. patent application Ser. No. 804,255 (European Laid-Open Patent Publication No. 0205046) filed by the present applicants disclose a monoclonal antibody specific to a complex of human protein C and a calcium ion bound to the Gla domain of human protein C and a method of separating human protein C using the monoclonal antibody.

It is an object of this invention to provide a method of separating activated human protein C.

Another object of this invention is to provide a method of separating activated human protein C using an antibody to a complex of human protein C and a calcium ion bound at the Gla domain on the basis of the surprising discovery of the fact that this antibody binds to activated human protein C.

Another object of this invention is to provide a method of very easily separating activated protein C having the Gla domain.

Another object of this invention is to provide a method of advantageously separating activated human protein C which is activated, has serine protease activity and is less stable than human protein C, without deactivating it.

Another object of this invention is to provide a method of easily obtaining highly pure activated human protein C from, for example, a mixture composed of human protein C activated by an enzyme and various impurities.

Another object of this invention is to provide a method of obtaining activated human protein C from a mixture of human protein C and activated human protein C independently from human protein C.

Further objects of this invention along with its advantage will become apparent from the following description.

According to this invention, the above objects and advantages are achieved by a method of separating activated human protein C, which comprises bringing a mixture containing activated human protein C having a gamma-carboxyglutamic acid (Gla) domain in the presence of a calcium ion into contact with a fixed antibody comprising an insoluble carrier and fixed thereto an antibody to a complex of human protein C and a calcium ion bound to the Gla domain whereby the activated human protein C is captured by the fixed antibody in the form in which the calcium ion is bound to the Gla domain.

The antibody used in this invention is an antibody to a complex of human protein C and a calcium ion bound to the Gla domain, specifically an antibody which does not recognize human protein C in which a calcium ion is not bound to the Gla domain, but recognizes human protein C having a calcium ion bound to the Gla domain.

The antibody may be monoclonal or polyclonal provided that it has the aforesaid properties. The monoclonal antibody is preferred in this invention because of the ease of mass production.

In the present invention, the antibody is fixed to an insoluble carrier. The insoluble carrier may be, for example, cellulose, agarose, crosslinked dextran, polyacrylamide, maleic acid polymer, porous glass, or a mixture of these. A method for fixing the antibody to such an insoluble carrier is known per se.

The following description is directed to the case of using monoclonal antibodies.

The monoclonal antibody can be produced by cultivating a hybridoma capable of producing the antibody to human protein C and separating and recovering the antibody to human protein C from the cultivation product.

The method of this invention is carried out by contacting a mixture containing activated human protein C having a Gla domain in the presence of a calcium ion with an antibody fixed to an insoluble carrier.

The above mixture may be, for example, a mixture obtained from the supernatant of the culture fluid of animal cells capable of producing activated human protein C, for example animal cells obtained by the recombinant technology (see, for example Japanese Laid-Open Patent Publication No. 111690/1987 and 29th Annual meeting of the American Society of Hematology, Summary 1400, 1987), or a mixture obtained by subjecting human protein C to a treatment of converting it into activated human protein C, for example, an enzyme treatment. Specifically, it may be, for example, a mixture containing activated human protein C obtain by activating human protein C obtained from a culture supernatant of animal cells which produce recombinant PC with thrombin, thrombin-thrombomodulin complex or snake venom, or a mixture containing recombinant activated human protein C obtained from a culture supernatant of animal cells which produce recombinant activated PC.

It will be clear from the above description that human protein C and activated human protein C, as referred to in this invention, may include both native and mutant forms so long as they have a Gla domain.

The concentration of a calcium ion in the presence of which the fixed antibody is contacted with a mixture containing activated human protein is desirably 0.1 mM to 50 mM, preferably 1 to 5 mM. Part of the calcium ion may, if desired, be replaced by another metal ion.

The above contacting may be carried out by a batch method or a column method.

Thus, according to the method of this invention, activated human protein C is captured by the fixed antibody in the form in which the calcium ion is bound to the Gla domain. Thereafter, the fixed antibody which captured activated human PC is usually washed fully in the presence of a calcium ion to remove unadsorbed protein impurities. Finally, it is treated with an aqueous medium substantially free from a calcium ion, preferably a buffered aqueous solution substantially free from a calcium ion, or a solution containing EDTA.

As a result, the activated human protein C can be separated and recovered from the fixed antibody in a form not binding the calcium ion in the Gla domain.

According to this invention, there is also provided a method of separating activated human protein C and human protein C independently from each other from a mixture containing the activated human protein C and the human protein C. Specifically, this invention provides a method of separating activated human protein C, which comprises (1) bringing a first mixture containing human protein C and activated human protein C having a Gla domain into contact with a first fixed antibody comprising an insoluble carrier and fixed thereto a first antibody to human protein C but not to activated human protein C to form a second mixture substantially free from human protein C while the human protein C is captured by the first fixed antibody, and (2) bringing the second mixture in the presence of a calcium ion into contact with a second fixed antibody comprising an insoluble carrier and fixed thereto a second antibody to a complex of human protein C and a calcium ion bound at the Gla domain whereby the activated human protein C is captured by the second fixed antibody in the form in which the calcium ion is bound to the Gla domain.

The antibody used in step (11 is an antibody to a human protein C but not to activated human protein C, which recognizes human protein C but does not recognize activated human protein C irrespective of whether a calcium ion is bound to the Gla domain.

The above antibody may be monoclonal or polyclonal so long as it has the above properties, but the monoclonal antibody is preferred in this invention.

The monoclonal antibody can be obtained by cultivating a hybridoma capable of producing an antibody to human protein C and separating and recovering from the cultivation product an antibody to human protein C but not to activated human protein C.

Such an antibody is fixed to the insoluble carrier and used in step (1). Contacting in step (1) is carried out irrespective of the presence or absence of a calcium ion.

According to step (1), human protein C is captured by the fixed antibody to form a mixture substantially free from human protein C.

It should be understood that the description of the invention initially made can be applied to the other items of step (1) and to all items of step (2).

Specific procedures of producing monoclonal antibodies that can be used in this invention will now be described in detail.

A. Isolation and purification of an antigen

Human protein C used as an antigen is isolated from human plasma and purified by the method of Suzuki et al., J. Biol. Chem., 258, 1914–1920 (1983).

B Immunization of a mouse with human protein C

Female BALB/c/ mice may be used, but mice of other strains may also be used. The immunizing plan and the concentration of human protein C should be selected so as to form a sufficient amount of antigenically stimulated lymphocytes. For example, a mouse is immunized intraperitoneally with 50 micrograms of human protein C three times at 2-week intervals, and finally 30 micrograms of human protein C is administered intravenously. Several days after the final immunization, the spleen cells are extracted from the animal for fusion.

C. Cell fusion

The spleen was aseptically taken out from the immunized mouse, and a suspension of the spleen cells was prepared. The spleen cells are fused with mouse myeloma cells from a suitable cell line in the presence of a suitable fusion promoter. The preferred ratio of the spleen cells to the myeloma cells is from about 20:1 to about 2:1, and a fusion medium is suitably used in an amount of 0.5 to 1.5 ml per about $10^8$ spleen cells.

The mouse myeloma cells used for cell fusion are well known. In the present invention P3-X63-Ag 8-U1cells (P3-U1) see D. E. Yelton et al., Current Topics in Microbiology and Immunology, 81, 1 (1978)) are used.

The fusion promoter is preferably polyethylene glycol having an average molecular weight of 1000 to 4000. Other fusion promoters known in the art can also be used. In the present invention, polyethylene glycol having an average molecular weight of 1540 is preferably used.

D. Selection of the fused cells

In a separate container (such as a microtiter plate), a mixture composed of the unfused spleen cells, unfused mouse myeloma cells and the fused hybridoma cells are diluted with a selective medium not supporting the unfused mouse myeloma cells, and cultured for a period sufficient to kill the unfused cells (about 1 week). A culture medium not supporting the unfused mouse myeloma cells, such as HAT medium, is used. In the selective medium, the unfused myeloma cells die. Since the unfused spleen cells are untransformed cells, they die away after a certain period of time (1 week). The fused cells, on the other hand, can survive in the selective medium since they have both the tumoral nature of the parent cells of myeloma and the nature of the parent spleen cells.

E. Determination of human protein C

After the hybridoma cells have thus been detected, the culture supernatant is sampled and screened for an antibody to human protein C by enzyme linked immunosorbent assay (ELISA). The assay is carried out by adding $CaCl_2$ in a certain concentration, for example 5 mM $CaCl_2$, to the culture supernatant, an enzyme-labelled antibody solution and a washing solution, and also in the absence of $CaCl_2$. Those hybridomas which prove to be positive only in the presence of $CaCl_2$ are selected. These hybridomas produce and secrete an antibody which does not recognize human protein C in the absence of a calcium ion but recognizes human protein C in the presence of a calcium ion.

F. Cloning of the hybridoma cells producing the desired antibody and the production of the antibody The hybridoma cells capable of producing the desired antibody are cloned by a suitable method such as a limiting dilution method, and the desired antibody can be produced by the following two different methods. According to a first method, the hybridoma cells are cultured in a suitable medium for a certain period of time, and the monoclonal antibody produced by the hybridoma cells can be isolated from the supernatant of the culture. According to a second method, the hybridoma cells are injected intraperitoneally into a syngenic or semisyngenic mouse. After a certain period of time, the monoclonal antibody produced by the hybridoma cells can be isolated from the blood and ascites of the host animal.

The following Examples illustrate the present invention more specifically.

EXAMPLE 1

Two female BALB/c/ mice (4 weeks old) were immunized with purified human PC four times at 14-day intervals. The first immunization was effected by intraperitoneally administering to the mice a mixture (emulsion) of 50 micrograms of human PC dissolved in phosphate buffer saline (PBS) and an equal volume of complete Freund's adjuvant in an amount of 0.5 ml/head. The second and third immunizations were effected by intraperitoneally administering to the mice a mixture of 50 micrograms of human PC and Freund's incomplete adjuvant. The final immunization was carried out by administering a PBS solution of 30 micrograms of human PC from the tail veins of the mice. Three days after the final immunization, the spleen cells of the immunized mice were used for cell fusion.

The spleen cells of the immunized mice and myeloma cells (P3U1) of a mouse of the same strain were mixed in a ratio of from about 2:1 to about 15:1 and fused in the presence of 50% polyethylene glycol 1540 (a product of Wako Pure Chemicals, Co., Ltd.) in accordance with the method of Köhler and Milstein. The fused cells were suspended in RPMI-1640 medium (containing 10% FCS) so that the concentration of the cells became $1\times10^6$ cells/ml. The suspension was distributed to the wells of a 96-well microplate (Coster) in an amount of 100 microliters per well.

The fused cells were incubated in a $CO_2$ incubator (5% $CO_2$, 37° C.). After one day, a medium containing hypoxanthine, aminopterin and thymidine (HAT media) was added to each well, and a half volume of the medium in each well was removed and the HAT medium was added to each well every second or third day. Thus, hybridoma cells composed of the spleen cells and the myeloma cells were screened.

The antibody in the culture supernatant of the hybridoma cells was detected by the ELISA method using a microtiter plate coated with human PC as an antigen. As a second antibody, an alkaline phosphatase-labelled rabbit anti-mouse IgG antibody was used, and to determine the difference of the binding of the antibody to human PC in the presence of a calcium ion from that in the absence of a calcium ion, TBS (0.02M Tris/HCl, 0.14M NaCl, pH 7.4) containing 5 mM $CaCl_2$ was added to one supernatant from one well, and TBS without CaCl was added to another supernatant from the same well. Furthermore, TBS containing 5 mM $CaCl_2$, 0.05% TWEEN 20 (polyethylene sorbitan monolaurate) 0.02% $NaN_3$, or TBS/0.05% Tween 20/0.02% $NaN_3$ was used as a diluent for the second antibody and a washing buffer.

In 541 wells in total in which the fused cells were plated, the formation of colonies was observed in 523 wells. Out of these, 44 wells were found to be positive in antibody production as shown in Table 1 below. Forty-four wells showed bonding to human PC in the presence of a calcium ion, and 32 wells showed binding to human PC in the absence of a calcium ion.

These positive wells were cloned twice by the limiting dilution method. The resulting cloned cells were suspended in 90% FCS-10% DMSO and stored in liquid nitrogen.

The monoclonal antibodies produced by the individual clones were proliferated in the abdominal cavities of BALB/c/ mice. Immunoglobulin was isolated from the ascites of the mice and purified by using a protein A-SEPHAROSE 4B (agarose carrier) column.

TABLE 1

| | |
|---|---|
| Number of wells in which the fusion cells were plated | 541 |
| Number of wells which formed colonies | 523 |
| Number of wells which produced antibodies | 44 |
| Binding to PC in the presence of $Ca^{++}$ was positive | 44 |
| Binding to PC in the absence of $Ca^{++}$ was positive | 32 |

IgG's of the individual clones purified from the mouse ascites were examined for subclasses, the effect on the expression of the activity of human PC, activity of binding to the L-chain or H-chain, and activity of binding to human PC whose Gla domain was removed by an enzyme treatment using alpha-chymotrypsin.

The subclasses were determined by the Ouchterlony method using anti-mouse antisera specific to the individual classes.

The effect on the expression of the activity of human PC was determined by mixing IgG and human PC in a mole ratio of 5:1, incubating the mixture overnight at 4° C. and activating incubated human PC by a thrombin-thrombomodulin complex, and determining the human PC activity by measuring the amidolytic activity using a synthetic substrate. As the synthesis substrate,

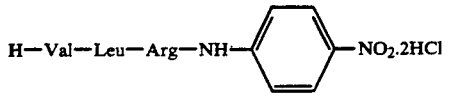

(in which Val represents optically active D-valine, Leu represents optically active L-leusine, and Arg represents optically active L-arginine; a product of Kabi Vitrum AB of Sweden designated as S-2266).

The activity of binding to the L-chain or H-chain was determined by subjecting human PC to electrophoresis under reducing conditions to separate the L- and H-chains, followed by immunoblotting using a nitrocellulose membrane and HRP-labelled goat anti-mouse IgG antibody.

The Gla domain-removed human PC was prepared by limited hydrolysis using alpha-chymotrypsin in accordance with the method of Esmon et al. N. L. Esmon et al., J. Bio. Chem., 258, 5548–5553 (1983)), and by immunoblotting, bondability of the antibodies to the Gla domain was determined.

The properties of the antibodies produced by the six clones are summarized in Table 2. The calcium ion-dependent antibodies all bound to the L-chain, and even in the presence of a calcium ion did not bind to human PC from which the Gla domain was removed. These antibodies were shown to recognize only that human PC which underwent conformational change dependent on the Gla domain to which the calcium ion binds.

TABLE 2

| Clone | Sub-class | Epitope on protein C (L-chain or H-chain) | $CA^{++}$ depend-ency | Bonding to the Gla domain-removed PC | Effect on PC activa-tion |
|---|---|---|---|---|---|
| 7B12 | $IgG_1$ | L | + | − | − |
| 10E12 | $G_1$ | L | + | − | − |
| 6H2 | $G_1$ | L | + | − | − |
| 6C3 | $G_2b$ | H | − | + | − |
| 10H11 | $G_1$ | H | − | + | + |
| 6B10-1 | $G_1$ | | − | + | − |

EXAMPLE 3

Bindability of monoclonal antibodies to PC and activated PC

Solid-phase immunoradiomeric assay was carried out by the method of Frankel et al. (Frankel et al.: Mol. Immunol., 16, 101–106, 1979), and dissociation constants (Kd) in reactions of binding of monoclonal antibodies to PC and activated PC were determined by the Scratchard analysis.

The results obtained with two anti-PC monoclonal antibodies are shown in Table.

TABLE 3

| | Kd | |
|---|---|---|
| IgG | PC | Activated PC |
| 6B10-1 | $6.86 \times 10^{-9}$M | $8.70 \times 10^{-9}$M |
| 10H11 | $5.10 \times 10^{-9}$ | — |

It was found that 10H11 is an antibody which does not bind to activated PC.

EXAMPLE 4

Fixation of an antibody to an insoluble carrier

Dry gel (0.3 g) of bromocyanogen-activated SEPHAROSE 4B (made by Pharmacia Fine Chemicals, Inc.) was swollen and washed with 100 ml of 1 mM HCl and further washed with a coupling buffer (0.1M $NaHCO_3$, pH 8.3, containing 0.5M NaCl). The coupling buffer was removed by suction, and immediately then, the gel was suspended in 2 ml of a coupling buffer containing antibody 6H2 (3 mg/ml). The suspension was slowly shaken overnight. The gel was then transferred to 2 ml of 1M ethanolamine-HCl pH 8.0), and the suspension was shaken at room temperature for 2 hours to block the remaining active groups. The antibody-bound SEPHAROSE gel (agarose carrier) was washed on a glass filter alternately with 0.1M acetate buffer (pH 4.0) containing 0.5M NaCl and 0.1M borate buffer containing 0.5M NaCl. When the absorbance at 280 nm of the fitrate became less than 0.01, it was equilibrated with 0.05M Tris/HCl (pH 7.4) containing 5 mM of $CaCl_2$ and 1 mM of benzamidine and filled in a column. As a result, antihuman PC monoclonal antibody 6H2-bound SEPHAROSE 4B column (to be referred to as 6H2 column) was prepared. In the same way as above an antihuman PC monoclonal antibody 10H11-bound column (to be referred to as 10H11 column) was prepared by using antibody 10H11. Activated PC was purified by using these 6H2 column and 10H11 column.

EXAMPLE 5

Purification of activated PC using a 6H2 column and a 10H11 column

A mixture (30 microliters) of thrombin (1.5U) and thrombomodulin and 300 microliters of 1% BSA-added buffer solution (0.05M Tris/HCl, 0.15M NaCl, 2.5 mM $CaCl_2$, pH=7.4) were added to 30 microliters of purified human PC (720 micrograms/ml), and the mixture was incubated at 37° C. for 90 minutes to activate PC.

The reaction was stopped by adding 20 microliters of Antithrombin III (ATIII) (20U). This reaction mixture (450 microliters) containing activated PC was first passed through a 10H11 column, and then successively through a 6H2 column. These columns had been equilibrated with a buffer solution (0.05M Tris/HCl, 0.15M NaCl, 5 mM $CaCl_2$, pH 7.4). The columns were washed with the same solution, and a buffer solution (0.06M Tris/HCl, 0.15M NaCl, 20 mM EDTA, pH 7.4) was passed through the 6H2 column to recover the adsorbed activated PC as a solution.

The solution was subjected to SDS polyacrylamide electrophoresis. It was determined that the recovered activated PC did not at all contain PC, and the recovery ratio measured from the activity was 62%.

What we claim is:

1. A method of separating activated human protein C, which has a gamma-carboxyglutamic acid (Gla) domain and is biologically active, from a mixture containing activated human protein C, which comprises bringing a mixture containing activated human protein C having a Gla domain in the presence of calcium into contact with a fixed monoclonal antibody comprising an insoluble carrier and fixed thereto a monoclonal antibody specific to a human protein C having a calcium ion bound to the Gla domain, whereby the activated human protein C having a calcium ion bound to the Gla domain is bound to the fixed monoclonal antibody, and then treating the fixed monoclonal antibody binding the activated human protein C having the calcium ion bound to its Gla domain with an aqueous medium substantially free from calcium ions, whereby the activated human protein C is released from the fixed antibody in a form not binding the calcium ion in the Gla domain.

2. The method of claim 1 wherein the aqueous medium is an aqueous medium containing EDTA.

3. The method of claim 1 wherein said mixture is from a culture supernatant of animal cells capable of producing activated human protein C.

4. A method of separating activated human protein C, which has a Gla domain and is biologically active, from a mixture containing activated human protein C and activated human protein C, which comprises:

(1) bringing a first mixture containing human protein C and activated human protein C having a Gla domain into contact with a fixed monoclonal antibody comprising an insoluble carrier and fixed thereto a first antibody specific to a human protein C but not to activated human protein C to obtain a second mixture substantially free from human protein C such that the human protein C is bound to the first fixed antibody.

(2) bringing the second mixture in the presence of calcium into contact with a second fixed monoclonal antibody comprising an insoluble carrier and fixed thereto a second antibody specific to human protein C having a calcium ion bound to the Gla domain, whereby the activated human protein C having a calcium ion bound to the Gla domain is bound to the second fixed monoclonal antibody, and then treating the second monoclonal antibody, and then treating the second monoclonal antibody capturing the activated human protein C having the calcium ion bound to its Gla domain with an aqueous medium substantially free from calcium ions, whereby the activated human protein C is separated from the second fixed antibody in a form not binding the calcium ion in the Gla domain.

5. The method of claim 4 wherein the aqueous medium is an aqueous medium containing EDTA.

6. The method of claim 4 wherein said first mixture from a culture supernatant of animal cells capable of producing human protein C is subjected to an activating step which comprises cleavage of the protein product with a protease selected from the group consisting of thrombin, thrombin-thrombomodulin complex, trypsin, and Russell's viper venom factor×activator.

7. The method of claim 6 wherein the animal cells are obtained by a gene recombination technique, which comprises transfecting the plasmid containing human protein C gene into the animal cells and selecting the cells which produce the activated human protein C.

8. The method of claim 4 wherein said first monoclonal antibody is 10H11.

9. The method of claim 4 wherein said second monoclonal antibody is 6H2.

* * * * *